United States Patent [19]

Effland

[11] 4,066,659
[45] Jan. 3, 1978

[54] METHOD OF PREPARATION OF 3-(3-CARBOXY-4-HYDROXYPHENYL)-4,5-DIHYDRO-2-PHENYLBENZ (E) INDOLE AND VALUABLE INTERMEDIATES RELATED THERETO

[75] Inventor: Richard C. Effland, Bridgewater, N.J.

[73] Assignee: American Hoechst Corporation, Bridgewater, N.J.

[21] Appl. No.: 692,331

[22] Filed: June 3, 1976

[51] Int. Cl.² .......................................... C07D 209/18
[52] U.S. Cl. ...................... 260/326.13 F; 260/293.62; 260/326.13 R; 260/326.8; 260/568; 260/570.5 CA; 260/583 R

[58] Field of Search ................................ 260/326.13 R

[56] References Cited

U.S. PATENT DOCUMENTS 3,845,073  10/1974  Newberry .................. 260/326.13 R Primary Examiner—Ethel G. Love
Attorney, Agent, or Firm—Curtis, Morris & Safford

[57] ABSTRACT

A novel method of preparing the valuable compound 3-(3-carboxy-4-hydroxyphenyl)-4,5-dihydro-2-phenylbenz[e]indole is described, said compound possessing antiinflammatory and analgetic activity. Also described are novel intermediates useful in the disclosed method.

14 Claims, No Drawings

METHOD OF PREPARATION OF 3-(3-CARBOXY-4-HYDROXYPHENYL)-4,5-DIHYDRO-2-PHENYLBENZ (E) INDOLE AND VALUABLE INTERMEDIATES RELATED THERETO

This invention relates to a method of preparation of 3-(3-carboxy-4-hydroxyphenyl)-4,5-dihydro-2-phenylbenz[e]indole, said compound being useful due to its antiinflammatory and analgesic activity. This invention further relates to the novel intermediates of the aforesaid method.

To the best of my knowledge the method and the intermediates thereof described herein have not heretofore been described or suggested. While several synthetic routes for the preparation of 3-(3-carboxy-4-hydroxyphenyl)-4,5-dihydro-2-phenylbenz[e]indole are described by Allen et al., U.S. Pat. No. 3,878,225, none relate to the method of the present invention. Furthermore, the facile reaction of a poorly nucleophilic amino group such as that of 5-aminosalicylic acid with an enamine is rather unexpected. The method described herein represents a preferred method inasmuch as it is a more economical way to produce the valuable 3-(3-carboxy-4-hydroxyphenyl)-4,5-dihydro-2-phenylbenz[e]indole.

The aforesaid patent describes the condensing of enamines with α-haloketones or aldehydes in a solvent such as dimethylformamide or toluene at a temperature of from 0° to 120° C., followed by hydrolysis to produce γ-diketones or γ-ketoaldehydes which can be further reacted to produce various pyrroles including 3-(3-carboxy-4-hydroxyphenyl)-2-phenyl-4,5-dihydrobenz[e]indole. While the above partially describes a general procedure whereby the novel intermediates of this method can be made, the patent does not teach or describe the presence or isolation of such intermediates or, even more importantly, their presently disclosed utility in my new method. As the prior art only describes a condensation reaction to prepare a third compound, there is no suggestion of any isolable or useful intermediate being produced in that procedure. Accordingly, the enammonium salts have now been effectively prepared, recognized, isolated and characterized for the first time and found especially suitable in a novel, preferred method for preparing valuable compounds.

I have now discovered that 3-(3-carboxy-4-hydroxyphenyl)-4,5-dihydro-2-phenylbenz[e]indole can be prepared by reacting 5-aminosalicylic acid with an enammonium salt which, in one of the possible tautomeric forms, is represented by the formula

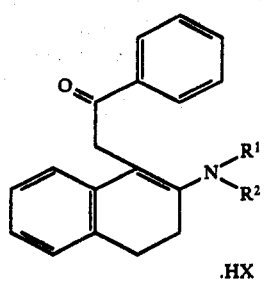

.HX wherein $R^1$ and $R^2$ are the same or different and each represents alkyl of from 1 to 6 carbon atoms or, together with the nitrogen atom to which they are attached, form a pyrrolidino, or piperidino ring and X is bromine or chlorine. The reaction is carried out in a solvent such as glacial acetic acid, 2-propanol or methanol and at a temperature of from about ambient to the boiling point of the solvent.

The enammonium salt is prepared by reacting a naphthalene compound of the formula

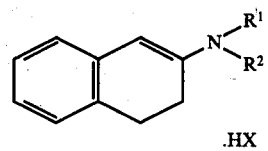

.HX in which $R^1$ and $R^2$ are as previously defined with phenacyl halide. This reaction can be carried out in dimethylformamide or toluene as a solvent at a temperature from about ambient to the boiling point of the solvent.

The method of this invention is further illustrated in greater detail in the examples below.

EXAMPLE 1 a. A solution of 500 g of phenacyl bromide in 700 ml of dimethylformamide is added dropwise to a stirring solution of 505 g of 2-(1-pyrrolidino)-3,4-dihydronaphthalene in 1300 ml of dimethylformamide. After total addition the reaction mixture is stirred for an additional 4.5 hours and then 1280 ml of ether are added. The precipitate is removed by suction filtration and washed successively with a dimethylformamide-ether (1:2) mixture and ether, leaving a white solid. The solid is dried under a vacuum to give 1-phenacyl-2-(1-pyrrolidino)-3,4-dihydronaphthalene hydrobromide, mp 217°-219° C.

b. 304 g of 5-aminosalicylic acid are added to 3800 ml of acetic acid while stirring. The stirred suspension is heated to 60° C. and 791 g of 1-phenacyl-2-(1-pyrrolidino)-3,4-dihydronaphthalene hydrobromide are added. An additional 150 ml of acetic acid are added to the reaction mixture, which is stirred at 70° C for 3 to 4 hours and then cooled to ambient temperature. A solid appears and is collected by filtration, washed successively with acetic acid and petroleum ether and dried for 16 hours under vacuum to give 3-(3-carboxy-4-hydroxyphenyl)-4,5-dihydro-2-phenylbenz[e]indole.

EXAMPLE 2

A well stirred mixture of 3.98 g of 1-phenacyl-2-(1-pyrrolidino)-3,4-dihydronaphthalene hydrobromide (Example 1a), 1.53 g of 5-aminosalicylic acid and 10 ml of acetic acid is heated at reflux for 15 minutes. The reaction mixture is allowed to stand at ambient temperature and then diluted with 10 ml of acetic acid. The resulting solid is collected by suction filtration, washed with 50 ml of petroleum ether and then dried under high vacuum for 72 hours to give 3-(3-carboxy-4-hydroxyphenyl)-4,5-dihydro-2-phenylbenz[e]indole.

EXAMPLE 3

A mixture of 1.92 g of 5-aminosalicylic acid and 5.0 g of 1-phenacyl-2-(1-pyrrolidino)-3,4-dihydronaphthalene hydrobromide (Example 1a), in 75 ml of methanol is refluxed under nitrogen for 9 hours. The solution is allowed to reach ambient temperature before being filtered. The methanol is removed under a vacuum to give a viscous oil which is dissolved in acetonitrile. This solution immediately crystallizes to give a yellow crystalline solid which is collected by filtration and washed with acetonitrile to give 3-(3-carboxy-4-hydroxyphenyl)-4,5-dihydro-2-phenylbenz[e]indole.

EXAMPLE 4 a. A mixture of 25 g of β-tetralone, 100 g of 4a molecular sieves in 400 ml of toluene is ice-bath cooled and then saturated with dimethylamine. The reaction mixture is stirred at 100° C for 4 hours, permitted to cool and then filtered. The toluene is evaporated off leaving a red oil which is vacuum distilled to give the yellow oil of 3,4-dihydro-2-naphthyl)-dimethylamine.

b. A solution of 22 g of phenacyl bromide in 50 ml of dimethylformamide is added dropwise to a stirring solution of 2-dimethylamino-3,4-dihydronaphthalene in 70 ml of dimethylformamide. After total addition the reaction mixture is stirred for an additional 5 hours and then 400 ml of ether are added. The white precipitate is collected, washed with ether and then dried. Recrystallization from acetonitrile gives the white solid, mp 145°–147° C, of 1-phenacyl-2-dimethylamino-3,4-dihydronaphthalene hydrobromide.

c. A mixture of 10.0 g of 1-phenacyl-2-dimethylamino-3,4-dihydronaphthalene hydrobromide and 4.1 g of 5-aminosalicylic acid in 50 ml of acetic acid is vigorously stirred at 75° C for 4.5 hours. The reaction mixture is then cooled to 20° C, filtered and the precipitate collected, washed successively with one 20 ml portion of acetic acid and five 20 ml portions of hexane and then dried for 20 hours under vacuum to give 3-(3-carboxy-4-hydroxyphenyl)-4,5-dihydro-2-phenylbenz[e]indole.

By following the method of Example 1a the treatment of 2-di-n-butylamino-3,4-dihydro-naphthalene, 2-diamylamino-3,4-dihydronaphthalene, 2-(1-piperidino)-3,4-dihydronaphthalene with phenacylbromide produces 1-phenacyl-2-di-n-butylamino-3,4-dihydronaphthalene hydrobromide, 1-phenacyl-2-diamylamino-3,4-dihydronaphthalene hydrobromide and 1-phenacyl-2-(1-piperidino)-3,4-dihydronaphthalene hydrobromide, respectively.

By following any of the methods of Examples 1b, 2 3 or 4, 3-(3-carboxy-4-hydroxyphenyl)-4,5-dihydro-2-phenylbenz[e]indole can be prepared from 1-phenacyl-2-di-n-butylamino-3,4-dihydronaphthalene hydrobromide or 1-phenacyl-2-(1-piperidino)-3,4-dihydronaphthalene hydrobromide.

By following the method of Example 4a, β-tetralone can be reacted with an amine to produce the naphthaleno compounds from which the corresponding enammonium salt is prepared.

I claim:

1. A method of preparing 3-(3-carboxy-4-hydroxyphenyl)-4,5-dihydro-2-phenylbenz[e]indole which comprises reacting an enammonium salt which, in one of the possible tautomeric forms, is represented by the formula

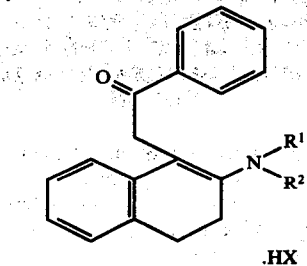

wherein $R^1$ and $R^2$ are the same or different and each represents alkyl of from 1 to 6 carbon atoms or, together with the nitrogen atom to which they are attached, form a pyrrolidino, or piperidino ring and X is bromine or chlorine with 5-aminosalicylic acid in a solvent and at a temperature of from about ambient to the boiling point of the solvent.

2. The method defined in claim 1 wherein the solvent is methanol, 2-propanol or glacial acetic acid.

3. The method defined in claim 2 wherein the solvent is methanol and the reaction is carried out under reflux.

4. The method defined in claim 3 wherein the enammonium salt is 1-phenacyl-2-(1-pyrrolidino)-3,4-dihydronaphthalene hydrobromide.

5. The method defined in claim 3 wherein the enammonium salt is 1-phenacyl-2-(1-piperidino)-3,4-dihydronaphthalene hydrobromide.

6. The method defined in claim 3 wherein the enammonium salt is 1-phenacyl-2-dimethylamino-3,4-dihydronaphthalene hydrobromide.

7. The method defined in claim 2 wherein the solvent is glacial acetic acid and the reaction is carried out at a temperature of from 70° to 80° C.

8. The method defined in claim 7 wherein the enammonium salt is 1-phenacyl-2-(1-pyrrolidino)-3,4-dihydronaphthalene hydrobromide.

9. The method defined in claim 7 wherein the enammonium salt is 1-phenacyl-2-(1-piperidino)-3,4-dihydronaphthalene hydrobromide.

10. The method defined in claim 7 wherein the enammonium salt is 1-phenacyl-2-dimethylamino-3,4-dihydronaphthalene hydrobromide.

11. The method defined in claim 2 wherein the solvent is glacial acetic acid and the reaction is carried out at reflux.

12. The method defined in claim 11 wherein the enammonium salt is 1-phenacyl-2-(1-pyrrolidino)-3,4-dihydronaphthalene hydrobromide.

13. The method defined in claim 11 wherein the enammonium salt is 1-phenacyl-2-(1-piperidino)-3,4-dihydronaphthalene hydrobromide.

14. The method defined in claim 11 wherein the enammonium salt is 1-phenacyl-2-dimethylamino-3,4-dihydronaphthalene hydrobromide.

* * * * *